(12) United States Patent
Pickart et al.

(10) Patent No.: US 9,586,989 B1
(45) Date of Patent: Mar. 7, 2017

(54) NON-TOXIC SKIN CANCER THERAPY WITH COPPER PEPTIDES

(75) Inventors: Loren R. Pickart, Bellevue, WA (US); Francoise D. Pickart, Bellevue, WA (US)

(73) Assignee: Skin Biology, Inc., Bellevue, WA (US)

( * ) Notice: Subject to any disclaimer, the term of this patent is extended or adjusted under 35 U.S.C. 154(b) by 0 days.

(21) Appl. No.: 13/445,782

(22) Filed: Apr. 12, 2012

Related U.S. Application Data

(60) Provisional application No. 61/474,670, filed on Apr. 12, 2011.

(51) Int. Cl.
C07K 4/12 (2006.01)

(52) U.S. Cl.
CPC ............ *C07K 4/12* (2013.01); *Y10S 514/887* (2013.01)

(58) Field of Classification Search
None
See application file for complete search history.

(56) References Cited

U.S. PATENT DOCUMENTS

| | | | |
|---|---|---|---|
| 5,164,367 A | 11/1992 | Pickart | |
| 5,382,431 A * | 1/1995 | Pickart | ........................ 424/401 |
| 5,554,375 A | 9/1996 | Pickart | |
| 5,888,522 A | 3/1999 | Pickart | |
| 5,902,786 A * | 5/1999 | Bregman | ..................... 514/15.2 |
| 6,858,201 B2 | 2/2005 | Pickart | |
| 2002/0107184 A1* | 8/2002 | Hirschman | ..................... 514/12 |

OTHER PUBLICATIONS

Beauchamp, E.M., et al., "Arsenic Trioxide Inihibits Human Cancer Cell Growth and Tumor Development in Mice by Blocking Hedgehog/GLI Pathway," Journal of Clinical Investigation 121(1):148-160, Jan. 2011.
Bilsland, A.E., et al., "Dynamic Telomerase Gene Suppression Via Network Effects of GSK3 Inhibition," PLoS ONE 4(7):1-17, Jul. 2009.
Goetz, T.E., et al., "Cimetidine for Treatment of Melanomas in Three Horses," Journal of the American Veterinary Medical Association 196(3):449-452, Feb. 1990.
Hong, Y., et al., "A 'Metastasis-Prone' Signature for Early-Stage Mismatch-Repair Proficient Sporadic Colorectal Cancer Patients and Its Implications for Possible Therapeutics," Clinical & Experimental Metastasis 27(2):83-90, Feb. 2010.
Kang, Y.A., et al., "Copper-GHK Increases Integrin Expression and p63 Positivity by Keratinocytes," Archives of Dermatological Research 301(4):301-306, Apr. 2009.
Kubecova, M., et al., "Cimetidine: An Anticancer Drug?" European Journal of Pharmaceutical Sciences 42(5):439-444, Apr. 2011.
Lamb, J., "The Connectivity Map: A New Tool for Biomedical Research," Nature Reviews: Cancer 7(1):54-60, Jan. 2007.
McCormack, M.C., et al., "The Effect of Copper Tripeptide and Tretinoin on Growth Factor Production in a Serum-Free Fibroblast Model," Archives of Facial Plastic Surgery 3(1):28-32, Jan.-Mar. 2001.
Pickart, L., "The Human Tri-Peptide GHK and Tissue Remodeling," Journal of Biomaterials Science: Polymer Edition 19(8):969-988, 2008.
Pickart, L., "The Human Tripeptide GHK (Glycyl-L-Histidyl-L-Lysine), The Copper Switch, and the Treatment of the Degenerative Conditions of Aging," in R. Klatz and R. Goldman (eds.), "Anti-Aging Therapeutics," American Academy of Anti-Aging Medicine, Chicago, 2009, vol. XI, Chap. 36, pp. 301-312 (reprint).
Pickart, L., and A. Margolina, "GHK-Copper Peptide in Skin Remodeling and Anti-Aging," SOFW Journal, 136:10-20, Jun. 2010.
Pickart, L., et al., "Inhibition of the Growth of Cultured Cells and an Implanted Fibrosarcoma by Aroylhydrazone Analogs of the Gly-His-Lys-Cu(II) Complex," Biochemical Pharmacology 32(24):3868-3871, Dec. 1983.
Sato, N., and A.H. Brivanlou, "Manipulation of Self-Renewal in Human Embryonic Stem Cells Through a Novel Pharmacological GSK-3 Inhibitor," Methods in Molecular Biology 331:115-128, 2006.
Siméon, A., et al., "Expression of Glycosaminoglycans and Small Proteoglycans in Wounds: Modulation by the Tripeptide-Copper Complex Glycyl-L-Histidyl-L-Lysine-$Cu^{2+}$·," Journal of Investigative Dermatology 115(6):962-968, Dec. 2000.
Song, E.Y., et al., "Glycogen Synthase Kinase-3β Inhibitors Suppress Leukemia Cell Growth," Experimental Hematology 38(10):908-921, Oct. 2010.
Wen, J., et al., "Effects of 6-Bromoindirubin-3'-Oxime on the Maintenance of Pluripotency of Porcine Embryonic Germ Cells in Combination With Stem Cell Factor, Leukemia Inhibitory Factor and Fibroblast Growth Factor," Reproduction 139(6):1039-1046, Jun. 2010.
Wu, K., et al., "9-cis-Retinoic Acid Suppresses Mammary Tumorigenesis in C3(1)-Simian Virus 40 T Antigen-Transgenic Mice," Clinical Cancer Research 6(9):3696-3704, Sep. 2000.

\* cited by examiner

*Primary Examiner* — Amber D Steele
*Assistant Examiner* — Schuyler Milton
(74) *Attorney, Agent, or Firm* — Wilson Sonsini Goodrich & Rosati

(57) ABSTRACT

Methods are provided for administering compositions for topical dermatological treatment and resolution of skin cancer lesions in humans and domestic animals, including especially light skinned individuals of equine, bovine, porcine, canine and other species susceptible to developing skin cancer. The compositions used to treat and resolve the skin cancer lesions generally comprise complexation of peptone digests of various proteins with copper(II) salts, indium(III) salts, tin(II) salts, and tin(IV) salts. These compositions adhere tightly to the lesion surface, strongly resist enzymatic breakdown by the cancerous tissue, and possess very strong tissue remodeling actions.

16 Claims, No Drawings

NON-TOXIC SKIN CANCER THERAPY WITH COPPER PEPTIDES

CROSS-REFERENCE TO RELATED APPLICATION

This application is based on U.S. Provisional Application No. 61/474,670, filed Apr. 12, 2011, which is incorporated herein by reference in its entirety.

BACKGROUND

Most conventional cancer therapies use an a priori assumption that surgical removal or lethal eradication with toxic drugs or radiation are the only effective therapies for treatment of cancers. However, there is evidence that relatively non-toxic compounds that promote cellular differentiation may revert cancerous cells to normal cells and stop or revert tumor growth. (Wu et al., Clin. Cancer Res., 6:3696-3704 (2000); Beauchamp et al., J. Clin. Invest. 121:148-160 (2011).) The goal in the latter approach is to not necessarily eradicate the cancerous cell, but rather to revert them to a slow growing, non-metastatic stage of differentiation that would allow patients to live a normal lifespan.

Skin cancers, such as basal cell carcinoma and melanomas, are currently treated by a variety of therapies such as radiation and toxic chemotherapeutic drugs. Most basal cell carcinomas are removed with surgery and/or treated with topical medication.

Melanoma Cancers in Humans

Melanoma skin cancer is a malignant tumor of melanocytes. Such cells are found predominantly in skin, but are also found in the bowel and the eye. Melanoma is one of the less common types of skin cancer, but causes the majority (75%) of skin cancer related deaths. Despite years of intensive research, early surgical resection of melanoma tumors still gives the greatest chance of cure but the recurrence rate is very high (up to 50%). Around 160,000 new cases of melanoma are diagnosed each year. It is diagnosed more frequently in women than in men, and is particularly common among Caucasians living in sunny climates, with high rates of incidence in Australia, New Zealand, North America, and northern Europe. According to a WHO report about 48,000 melanoma related deaths occur worldwide per year.

The treatment typically includes surgical removal of the tumor, adjuvant treatment, chemo- and immunotherapy, or radiation therapy.

Malignant Melanoma in Horses

Skin cancer melanomas in horses are actually a relatively common affliction, particularly for older horses with dilute coat color (white or gray), but can occur in horses of any age. This is why the term "gray horse melanoma" has become part of the common vocabulary for horse owners, breeders and competitors.

Gray horses appear in many breeds such as the Thoroughbred, the Arabian, the American Quarter Horse, the Percheron, the Andalusian, the Welsh pony, and Lipizzaner. Published literature indicates that up to 80% of white or gray horses will develop melanomas by the age of 15 years. The most common sites for melanomas to grow are under the tail and around the anus, in the groin, and in the neck at the site of the parotid salivary glands. The melanomas tend to grow as a hard nodule or lump in the skin.

Melanomas occur in horses of all colors, but they are seen most commonly in gray and white horses older than six years of age. Approximately 80% of gray colored horses older than 15 years of age are affected by melanomas. The gray hair color is controlled by a single dominant gene that regulates specific kinds of stem cells and also enhances the risk for melanoma in horses. Horse melanomas can occur anywhere on the body and can be hard, soft, solitary, or multiple. Often they are located subcutaneously and are covered by normal haired skin, however, with time, they may become ulcerated and infected. Clinically, equine melanomas grow slowly for 10-15 years without metastasis, then suddenly become metastatic and invade internal organs.

Basal Cell Cancers in Humans

Basal cell carcinomas are called keratinocyte carcinomas or keratinocyte cancers. The cells of these cancers share features with the cells in the lowest layer of the epidermis, called the basal cell layer. About 8 out of 10 skin cancers are basal cell carcinomas which usually develop on sun-exposed areas, especially the head and neck. Basal cell carcinoma is primarily found in middle-aged or older people. It is very rare for a basal cell cancer to spread to nearby lymph nodes or to distant parts of the body. But if a basal cell cancer is left untreated, it can grow into nearby areas and invade other tissues beneath the skin.

Tissue Remodeling and Cancer Inhibition

A non-toxic method that suppresses skin cancers without requiring surgery or toxic therapies would represent a significant advance in the art. Many clinicians in the field are of the opinion that cancer surgeries often increase the spread of cancer. (Retskya et al., Int. J. Surg. 3:179-187 (2005).) Chemotherapies often produce many types of collateral tissue damage.

It is believed that skin repair has two distinct phases. There is an initial inflammatory, wound closure phase of a few days to a few weeks during which cells migrate into the wound area and there is extensive tissue rebuilding and scar formation. During this time, a human tripeptide (GHK or Gly-L-His-L-Lys) is generated. (Pickart, J. Biomater. Sci. Polymer Edn. 19:969-988 (2008); Pickart, Therapeutics, 11:301-312 (2009); Pickart and Margolina, SOFW Journal, 136:10-20 (2010).) GHK has an extraordinary affinity for copper 2+ and can obtain copper 2+ from its transport site on human albumin thus forming GHK-Cu (Gly-L-His-L-Lys:copper 2+).

As GHK-Cu accumulates, it shuts down the initial inflammatory wound healing phase and acts to restore a normal skin morphology by removing scar tissue, and rebuilding nerve and vascular networks. Studies of GHK-Cu in mice, rats, pigs, and humans found it to possess regenerative, anti-inflammatory, and anti-infection properties. Recent studies revealed a new array of GHK's activities, including stem cell activation (Kang et al., Arch. Dermatol. Res. 301(4):301-306 (2009)), repair of damaged DNA and restoration of cellular functions after radiation damage (McCormack et al., Arch. Facial Plast. Surg. 3:28-32 (2001)).

GHK, at 1 micromolar, has been reported to suppress messenger RNA production in human cancer associated genes. (Hong et al., Clin. Exp. Metastasis, 27:83-90 (2010).) GHK was the most potent cancer gene suppressor found, out of 1309 bioactive compounds (including many anti-cancer drugs), by using the Broad Institute's Connectivity Map which measured GHK's effects on messenger RNA production on all human genes. (Lamb, Nat. Rev. Cancer, 7:54-60 (2007).) GHK was found to be a substance that suppressed RNA production in 70% of 54 human genes overexpressed in patients with aggressive metastatic form of colon cancer. Hong, et al. used genome-wide profiling to identify genetic biomarkers (genetic signature) for metastasis prone colorectal cancer as well as their perturbagens—substances that modulated their expression. The search yielded only two substances that were able to downregulate expression of "metastatic" genes—GHK and plant alkaloid securinine. GHK produced results at a low non-toxic 1 micromolar concentration, and securinine at 18 micromolar. Suppression of the cancer genes occurred with GHK without copper 2+ and did not demonstrate actual inhibition of cancer growth in cell cultures or in animals. GHK may act by binding copper 2+ and then inhibiting cancer genes by increasing production of decorin, a proteoglycan (Simeon et al., *J. Invest. Dermatl.* 115(6):962-968 (2000)). Decorin's regenerative and anti-inflammatory actions (regenerating nerves and muscles, suppressing scar formation) are similar in some respects to those of GHK. Studies have found decorin to suppress tumor growth and metastasis of cancerous tissue (breast, prostate, osteosarcoma) in animal models. Ständer et al., *Cell Tissue Res.* 296(2):221-227 (1999); Goldoni et al., *Am. J. Pathol.* 173(3):844-955 (2008).

It may seem contradictory that GHK both supports and activates adult stem cells and also suppresses cancer genes. However, the information on GHK in the Broad Institute's Connectivity Map database lists drug compounds that are the most similar to GHK in terms of effects on messenger RNA production of various genes. The second most similar compound is 6-bromoindirubin-3'-oxime. This compound also keeps stem cells functioning (Wen et al., *Reproduction*, 139(6):1039-1046 (2010); Sato and Brivanlou, *Meths. Mol. Biol.* 331:115-128 (2006)) and suppresses cancer growth in animals by suppressing telomerase activity. Song et al., *Exp. Hematol.* 38(10):908-921 (2010); Bilsland et al., *PLoS One*, 4(7):e6459 Jul. 31 (2009). GHK may also act as an inhibitor of telomerase since the Broad Institute's Chem Bank reports that GHK has a high affinity for human telomerase.

Metastatic cancer cells may activate the same migration-inducing genes utilized in the early stage of wound healing which requires rapid migration of repair cells into the wounded region. Since the later remodeling stage shuts down this migration, substances that promote skin remodeling may act by downregulating the migration/metastasis genes.

Tissue remodeling is a key process in the inhibition of cancer growth. Strong tissue remodeling produces healthy tissues. In children, remodeling is very high and most accidental scars quickly vanish. But during the decades of aging, remodeling declines. Less vigorous remodeling produces various skin blemishes ranging from sun damage, hyperpigmentations, residual scars, calluses, skin tags, moles. Finally, at a low level of remodeling, localized cancers more easily grow and metastatic cancers thrive. If remodeling is defined as Regenerative Homeostasis, that is, the maintenance of healthy tissue growth, then Regenerative Homeostasis can be viewed as a spectrum ranging from normal healthy regeneration to increasing unhealthy forms of regeneration. In this sense, metastatic cancer is the most extreme example of an unhealthy response.

Cimetidine, commonly prescribed for gastric and duodenal ulcer disease, is a histamine H2-receptor antagonist. Cimetidine is often used to treat equine melanomas. Goetz et al., *J. Am. Vet. Med. Assoc.* 196:449-452 (1990). Cimetidine has structural similarities to GHK, and also has a high binding affinity for copper 2+. Pickart, *J. Biomater. Sci. Polymer Edn.* 19:69-988 (2008). Cimetidine has also been advocated as a treatment for a number of dermatological diseases. There is extensive research on the potential use of cimetidine as an anti-cancer therapeutic. Kubecova et al., *Eur. J. Pharm. Sci.*, Feb. 15 (2011).

In 1983, Linus Pauling's group reported a method of using copper peptides as an anti-cancer agent in mice treated with cancerous Ehrlich ascites cells which causes the death of the mice within 60 days. They used treatment by injection for 12 days of a mixture of 8 micrograms of ascorbic acid (vitamin C) and 8 micrograms copper 2+ complexed to Glycyl-Glycyl-L-Histidine. They found that injection of this mixture prolonged the life span of 60% of the mice inoculated with Ehrlich tumor cells. The remaining 40% of the mice lived for a long time and attempts to re-establish the tumor cells in these mice failed, suggesting that the mice became resistant to the cancer. Kimoto et al., *Cancer Res.*, 43:823-834 (1983). Pauling had long asserted that vitamin C ingestion in modem humans is too low and recommended that humans ingest 5 grams of vitamin C daily based in part on what similar primates ingest in a jungle habitat.

Using GHK-copper as the copper complex, mice were implanted with a mouse fibrosarcoma that grows within muscles as a solid tumor. Pickart et al., *Biochem. Pharmacol.* 32:3868-3871 (1983). Control mice were injected intraperitoneally (I.P.) with physiological saline three times per week. The treatment group was injected I.P. with 8 micrograms of GHK-copper 2+ and 8 micrograms ascorbic acid three times a week. After six weeks, the tumor size was determined. The tumor size in the control mice was the largest. The group treated with GHK-copper 2+ plus ascorbic acid was reduced by 78% in comparison to the control mice. ($p<0.005$ in comparison to the control mice.) The methods appeared to have no toxic effects on the mice.

SUMMARY OF THE INVENTION

The present invention provides compositions and methods for treating skin cancer lesions by resolving the lesion or inhibiting further development in warm-blooded mammals susceptible to the development of such cancers. The compositions useful in these methods, including pharmaceutical compositions, are prepared from combinations of ionic metals, such as copper or tin ions, and ionic metal-binding organic molecules, such as peptides and peptone compositions.

Thus, the present invention provides therapeutic and even preventative treatments for a variety of skin cancers by the use of, e.g., copper or tin ions, and ionic metal-binding organic molecules. These actions are attained with compositions formulated at the normal pH ranges of the human tissues, that is between about 5.0 and about 7.5. The skin cancer lesion may be a basal or squamous cell carcinoma, malignant melanoma, dermatofibrosarcoma protuberans, Merkel cell carcinoma, Kaposi's sarcoma, keratoacanthoma, spindle cell tumor, sebaceous carcinoma, microcystic adnexal carcinoma, atypical fibroxanthoma, leimyosarcoma, or angiosarcoma.

The present compositions and methods typically employ formulations of ionic metals and other metal-binding molecules, including but not limited to formulations of short peptides and mixtures thereof, such as peptones complexed with the ionic metals. The peptone is typically a peptone digest prepared from casein, collagen, elastin, meat protein, silk protein, or soybean protein. The ionic metal complexed with the peptone digest is typically copper(II), indium(III), tin(II) or tin(IV). The methods comprise administering to a human or other mammal a therapeutically or prophylactically effective amount of a composition, which comprises the organic metal complex and a physiologically acceptable carrier, to the area containing the skin cancer lesion or area susceptible to development of such a lesion. In humans, this would typically correspond to about 50-150 mg administered daily, twice daily, or three to four times per week, as necessary to accomplish the intended treatment result, to resolve the lesion or inhibit lesion development. Duration of administration will typically be for several weeks or more until the lesions have regressed and preferably have resolved. This dosage regimen is substantially below levels where adverse effects of the ionic metal and binding molecule complexes could prove troublesome.

In preferred embodiments the method is directed to resolving or inhibiting development of a melanoma lesion on a horse, by administering to the lesion a composition of peptone-ionic metal complex and a topically acceptable carrier in an amount and for a duration sufficient to resolve or inhibit the lesion. In another embodiment exemplified herein, the method concerns resolving or inhibiting the development of a basal cell carcinoma lesion on an individual by applying to the lesion a peptone-ionic metal complex and a topically acceptable carrier in an amount and for a duration sufficient to resolve the lesion. The lesion may be a site of a prior surgical removal of the carcinoma.

DESCRIPTION OF THE SPECIFIC EMBODIMENTS

The present invention provides methods for resolving or reducing skin cancer lesions on an individual by using non-toxic compositions of ionic metals complexed with ionic metal-binding organic molecules, such as peptones and short peptides. Small peptide copper complexes such as GHK-copper or Gly-Gly-His-copper can be used to induce anti-cancer actions, although defined peptides also potentially have drawbacks. First, they are easily destroyed by the enzymes released from cancer cells. Tumors spread through tissue by releasing enzymatic proteases that degrade proteins and peptides in the surrounding tissue. GHK is very quickly broken down when exposed to minute amounts of enzymes with carboxypeptidase activity. Second, these small defined peptides may have poor adhesion to skin or skin cancers and require complicated creams and lotion to force them into the skin. Finally, their tissue remodeling actions are only moderately strong.

A better choice of peptides to complex with ionic metals such as copper 2+ are those found in the mixed peptides of peptone digests which are the generated by, e.g., enzymatic proteolysis of proteins and peptides and as such, are very resistant to further digestion. These mixed peptide-metal complexes also adhere tightly to skin and are similar to the same mixed peptides that have found use in collagen glues. Finally, they produce much stronger remodeling responses than GHK or the many other small defined peptides described in previous patents.

Methods of preparing these mixed peptide ionic metal complexes and formulating them are generally described in, e.g., U.S. Pat. Nos. 5,382,431, 5,554,375, and 5,888,522, each of which is incorporated herein by reference.

Peptones are generally comprised of intermediate polypeptide products and mixtures of small peptides, formed in partial hydrolysis of proteins. Among the types of protein digests useful in the invention are digests of soybean protein, casein, collagen, elastin, meat products (e.g., PRIMATONE®), such as beef, liver, silk protein and so forth. By peptone digest is meant that the protein is degraded by enzymatic digestion or by acid or base hydrolysis, according to well known procedures, such as described in Remington's Pharmaceutical Sciences, Mack Publishing Co., Easton, Pa. pp. 428-429 (1975), which is incorporated herein by reference, using enzymes such as papain, etc. Alternatively, the digests may be produced by bacterial or yeast cultures that internally hydrolyze proteins and secrete the subsequent peptides, or by bacterial cultures that secrete hydrolytic enzymes into a culture medium which then hydrolyze proteins in the culture medium. Many peptone digests are widely available commercially, such as from Sigma Chemical Company, St. Louis, Mo.

In particular variations, the peptide or peptide derivative complexed with the ionic metal is, or includes, any one of the following:

Glycyl-histidyl-lysine, glycyl-histidyl(1-methyl)-lysine, glycyl(3-methyl)-histidyl-lysine, lysyl-histidyl-glycine, lysyl-histidyl(1-methyl)-glycine, lysyl(3-methyl)-histidyl-glycine, glycyl-histidyl-glycine, alanyl-histidyl-lysine, or valyl-histidyl-lysine.

For example, in some embodiments, the peptide or peptide derivative has the formula $R_1$-glycyl-histidyl-lysine-$R_2$, $R_1$-glycyl(3-methyl)-histidyl-lysine-$R_2$, $R_1$-lysyl-histidyl-glycine-$R_2$, $R_1$-lysyl-histidyl(1-methyl)-glycine-$R_2$, $R_1$-lysyl(3-methyl)-histidyl-glycine-$R_2$, or $R_1$-glycyl-histidyl-glycine-$R_2$, where $R_1$ is, e.g., any one of the following groups: a hydrogen; an —$NH_2$ moiety; an alkyl moiety containing from 1 to 18 carbon atoms; an aryl moiety containing from 6 to 12 carbon atoms; an alkoxy moiety containing from 1 to 18 carbon atoms; an aryloxy moiety containing from 6-12 carbon atoms; an aminoalkyl moiety containing from 1 to 18 carbon atoms; tryptophan; (glycyl)$_y$-tryptophan, wherein y=1-4; prolyl-$X_1$-phenylalanyl-$X_2$, wherein $X_1$ and $X_2$ are selected from the group consisting of valine, alanine, and glycine, and wherein $X_1$ and $X_2$ are not both valine; $X_1$-phenylalanyl-$X_2$, wherein $X_1$ and $X_2$ are selected from the group consisting of valine, alanine, and glycine, and wherein $X_1$ and $X_2$ are not both valine; $(X_3)_n$-tryptophan, wherein $X_3$ is a —$CH_2$— or —CH(OH)— moiety and n=4-20; and $(X_4)_n$, wherein $X_4$ is glucose, mannose, galactose, glucosamine, or galactosamine and n=1-5; and where $R_2$ is, e.g., any one of the following groups: prolyl-valyl-phenylalanyl-valine; valyl-phenylalanyl-valine; an alkyl moiety (e.g., an alkyl moiety containing from 1 to 18 carbon atoms); an aryl moiety (e.g., an aryl moiety containing from 6 to 12 carbon atoms); an alkoxy moiety (e.g., an alkoxy moiety containing from 1 to 12 carbon atoms); an aryloxy moiety (e.g., an aryloxy moiety containing from 6 to 12 carbon atoms); an aminoalkyl moiety (e.g., an aminoalkyl moiety containing from 1 to 18 carbon atoms); tryptophan; (glycyl)$_y$-tryptophan, where y=1-4; prolyl-$X_1$-phenylalanyl-$X_2$ or $X_1$-phenylalanyl-$X_2$, where $X_1$ and $X_2$ are each independently selected from the group consisting of valine, alanine, and glycine, and $X_1$ and $X_2$ are not both valine; $(X_3)_n$-tryptophan, where $X_3$ is a —$CH_2$— or —CH(OH)— moiety and n=4-20; $(X_4)_n$, where $X_4$ is a naturally occurring carbohydrate (e.g., glucose, mannose, galactose, glucosamine, or galactosamine) and n=1-5; an $NH_2$ moiety; an alkylamino moiety (e.g., an alkyl amino moiety containing from 1 to 18 carbon atoms); and (glycyl)$_n$-tryptophan, wherein n=1-2.

In other variations, the peptide or peptide derivative has the formula $R_1$—X-lysyl-histidyl(1-methyl)-glycine-$R_2$, $R_1$—X-histidyl-lysine-$R_2$, or $R_1$—X-histidyl-glycine-$R_2$, where X is a dipeptide moiety comprising glycine (e.g., glycyl-alanyl, glycyl-seryl, or glycyl-valyl); $R_1$ is as set forth above; and $R_2$ is an alkyl moiety (e.g., an alkyl moiety containing from 1 to 18 carbon atoms); an aryl moiety (e.g., an aryl moiety containing from 6 to 12 carbon atoms); an alkoxy moiety (e.g., an alkoxy moiety containing from 1 to 18 carbon atoms); an aryloxy moiety (e.g., an aryloxy moiety containing from 6 to 12 carbon atoms); prolyl-valyl-phenylalanyl-valine; or valyl-phenylalanyl-valine.

Other suitable peptides or peptide derivatives for use in accordance with the present invention include those having the formula $R_1$—X—$R_2$—$R_3$—$R_4$, $R_1$—$R_2$—X—$R_3$—$R_4$, or $R_1$—$R_2$—$R_3$—X—$R_4$, where X is glycine or alanine, $R_1$ is as set forth above, and $R_2$ and $R_3$ are each a basic amino moiety. Particularly suitable basic amino moieties include, for example, basic amino acids (e.g., histidine, lysine, or arginine), modified basic amino acids (e.g., (3-W)-histidine or (5-W)-histidine, where W is an alkyl moiety containing from 1 to 12 carbon atoms or aryl moiety containing from 6-12 carbon atoms), or —NHCH(($CH_2$)$_n$$NH3^+$)CO—, where n=5-10. Typically, $R_4$ is any one of the following groups: a hydrogen; an —$NH_2$ moiety; an alkyl moiety (e.g., an alkyl moiety containing from 1 to 18 carbon atoms); an aryl moiety (e.g., an aryl moiety containing from 6 to 12 carbon atoms); an alkoxy moiety (e.g., an alkoxy moiety containing from 1 to 18 carbon atoms); an aryloxy moiety (e.g., an aryloxy moiety containing from 6-12 carbon atoms; an aminoalkyl moiety (e.g., an aminoalkyl moiety containing from 1 to 18 carbon atoms); tryptophan; (glycyl)$_y$-tryptophan, where y=1-4; prolyl-$X_1$-phenylalanyl-$X_2$ or $X_1$-phenylalanyl-$X_2$, where $X_1$ and $X_2$ are valine, alanine, or glycine and $X_1$ and $X_2$ are not both valine; ($X_3$)$_n$-tryptophan, where $X_3$ is a —$CH_2$— or —CH(OH)— moiety and n=4-20; and ($X_4$)$_n$, where $X_4$ is a naturally occurring carbohydrate (e.g., glucose, mannose, galactose, glucosamine, or galactosamine) and n=1-5.

In particular variations, the peptide or peptide derivative as set forth above has the formula $R_1$-glycine-$R_2$—$R_3$—$R_4$, $R_1$—$R_2$-glycine-$R_3$—$R_4$, $R_1$—$R_2$—$R_3$-glycine-$R_4$, or $R_1$-alanine-$R_2$—$R_3$—$R_4$.

In yet other embodiments, the peptide or peptide derivative has the formula $R_1$—$R_2$—$R_3$—$R_4$, where $R_1$ is as set forth above, $R_2$ is an amino acid or amino acid derivative, $R_3$ is a basic amino acid (e.g., histidine, lysine, or arginine); and $R_4$ is a chemical moiety joined to $R_3$ by an amide bond. In specific variations, $R_4$ is an —$NH_2$ moiety, an alkylamino moiety (e.g., an alkylamino moiety having from 1-20 carbon atoms), or an arylamino moiety (e.g., an arylamino moiety having from 6-20 carbon atoms).

In yet other variations, the peptide or peptide derivative has the formula $R_1$—$R_2$—$R_3$—$R_4$—$R_5$, where $R_1$ is as set forth above; $R_2$, $R_3$, and $R_4$ are each a basic amino moiety; and $R_5$ is, e.g., any one of the following groups: a hydrogen; an —$NH_2$ moiety; an alkyl moiety (e.g., an alkyl moiety containing from 1 to 18 carbon atoms); an aryl moiety (e.g., an aryl moiety containing from 6 to 12 carbon atoms); an alkoxy moiety (e.g., an alkoxy moiety containing from 1 to 18 carbon atoms); an aryloxy moiety (e.g., an aryloxy moiety containing from 6-12 carbon atoms); an aminoalkyl moiety (e.g., an aminoalkyl moiety containing from 1 to 18 carbon atoms); tryptophan; (glycyl)$_y$-tryptophan, where y=1-4; prolyl-$X_1$-phenylalanyl-$X_2$ or $X_1$-phenylalanyl-$X_2$, where $X_1$ and $X_2$ are valine, alanine, or glycine and $X_1$ and $X_2$ are not both valine; ($X_3$)$_n$-tryptophan, where $X_3$ is a —$CH_2$— or —CH(OH)— moiety and n=4-20; and ($X_4$)$_n$, where $X_4$ is a naturally occurring carbohydrate (e.g., glucose, mannose, galactose, glucosamine, or galactosamine) and n=1-5.

Particularly suitable peptides having the formula $R_1$—$R_2$—$R_3$—$R_4$—$R_5$, as set forth above, include those in which $R_2$ is lysine or —NHCH(($CH_2$)$_n$$NH3^+$)CO—, where n=5-10; $R_3$ is histidine, (3-W)-histidine, or (5-W)-histidine, where W is an alkyl moiety containing from 1 to 12 carbons atoms or an aryl moiety containing from 6-12 carbon atoms; and/or $R_4$ is a basic amino acid or a modified basic amino acid. In accordance with any of the peptide-metal complexes described above, the following aryl, alkyl, aryloxy, and alkoxy moieties are particularly suitable: aryl: benzyl; alkyl: methyl, unbranched alkyl (e.g., n-octyl), and N-stearyl; aryloxy: O-benzyl; and alkoxy: methoxy, n-palmityl, n-stearyl, and unbranched alkyl (e.g., n-octyl).

In certain embodiments, a chelating agent may be added to the peptide-metal complex to form a ternary peptide-metal-chelating agent complex. Suitable chelating agents include imidazole or imidazole-containing compounds (e.g., histidine) and sulfur containing amino acids (e.g., cysteine or methionine). Thus, if the peptide-metal complex is glycyl-histidyllysine: copper(II), histidine may be added to yield the ternary complex glycyl-histidyllysine: copper(II): histidine. To form such a ternary complex, the molar ratio of metal to peptide to chelating agent is considered. For example, if the ratio of peptide to metal is 2:1, the addition of a chelating agent to the peptide-metal complex, although possible, is difficult due to site occupancy by the peptide. By maintaining the ratio of peptide to metal near 1:1, a chelating group is readily added to form the ternary complex. Preferably, the peptide to metal to chelating agent ratio is about 1:1:1.

Ionic metal complexes of copper, tin and zinc, or the salts thereof, such as sulfate, acetate, phosphate, gluconate, di-D-gluconate, acetyl tyrosinate, asparatate, methylsilanol, acetylmethionate, bis(N-acetyl-1-methioninato-, PCA (L-proline, 5-oxo-), PCA methysilanol, usnate (1,3-(2H, 9bh)-dibenzofurandione, 2,6-diacetyl-7,9-dihydroxy-8,9b-dimethyl-) and other complexing agents, are useful in preparing compositions used in the methods of the present invention.

To produce the complexes useful in the present invention, the peptides are complexed with one or more ionic transition metals, such as copper, tin, zinc, or the salts thereof, such as sulfate, acetate, phosphate, etc. In one method for preparing the organic-metal complex, the peptide is dissolved in warm water (about 40° C. to 60° C.) at a concentration of about 20 to 50% (weight/volume), then mixed with an aqueous solution of a metal salt complex at a salt concentration of about 10 to 50% (w/v). General methods for preparing metal-organic complexes and compositions thereof that can be used in the present invention are described in U.S. Pat. Nos. 5,164,367; 5,888,522; and 6,858,201, each of which is incorporated herein by reference in its entirety.

To form combinations of metal-organic complexes, a organic copper binding molecule is combined with an amount of an aqueous solution of transition metal salt sufficient to form a complex. Typically the complex is then combined with a pharmaceutically acceptable carrier to form a cream, lotion, or solution in a concentration of from about 0.1% to about 25% peptide-metal complex or more. The preparation may be sterilized or pasteurized, as desired, without destroying the activity of the peptide-metal complex.

By complexed is meant that the ionic metal (e.g., copper) binding molecule, such as a peptide or peptone preparation, and metal ions form electrostatic bonds, although this mechanism is offered only by way of possible explanation only and not by way of limitation.

The pH of the mixture is adjusted (with sodium hydroxide or other acceptable agent) to a pH between 5.0 and 7.0, typically about 7.0. Depending on the method of administration, which could be topically via cream, paste, salve, lotion, ointment, spray, emulsion, aerosol, via site-specific injection, incorporation into dermal patches, a gel, or other means of well known topical delivery systems and appropriate delivery vehicles.

For administration to warm-blooded animals, the peptide-metal compositions can be sterilized and incorporated in pharmaceutical or veterinary formulations. Such compositions can be sterilized by conventional, well-known sterilization techniques, e.g., boiling or pasteurization, without substantially adversely affecting the biological activity of the peptide-metal complexes. The compositions may contain pharmaceutically and dermatologically acceptable auxiliary substances and carriers as required to approximate physiological conditions and as necessary to prepare compositions for convenient administration, such as pH adjusting and buffering agents, and delivery vehicles. Actual methods for preparing pharmaceutically administrable compounds will be known or apparent to those skilled in the art and are described in detail in, for example, Remington's Pharmaceutical Science, supra.

For semi-solid compositions, as would be appropriate for pastes, creams and gels intended for topical administration to the skin, the peptide-metal complexes can be provided separately or may be compounded with other agents, and may include nontoxic carriers such as, for example, aloe vera gel, squalane, glycerol stearate, polyethylene glycol, cetyl alcohol, stearic acid, and propylene glycol, among others. Such embodiments may contain additional ingredients to impart the desired texture, consistency, viscosity, or appearance. Such additional ingredients are familiar to those skilled in the art and include emulsifying agents such as non-ionic ethoxylated and nonethoxylated surfactants, fatty alcohols, fatty acids, organic or inorganic bases, preserving agents, wax esters, steroid alcohols, triglyceride esters, phospholipids such as lecithin and cephalin, polyhydric alcohol esters, fatty alcohol esters, hydrophilic lanolin derivatives, hydrophilic beeswax derivatives, hydrocarbon oils such as palm oil, coconut oil, mineral oil, cocoa butter waxes, silicon oils, pH balancers, and cellulose derivatives. Penetration-enhancing agents include, for example, dimethylsulfoxide (DMSO), urea, and eucalyptol.

Such compositions will typically contain about 1-50% active ingredient of ionic metal-peptides, more preferably about 1-25%. Thus, the final concentration of copper or other metal in a formulation can range from about 0.1 or 0.15% (w/v) up to 0.4 to 0.8% or 1.6%, and in some instances up to 2 to 5% or more, although it will typically be desirable to employ the lowest final concentration as possible which achieves the desired effect. In the case of a liquid pharmaceutical preparations to be applied topically, the concentration of penetration enhancing agent such as DMSO may comprise, e.g., about 30% to about 80% of the pharmaceutical preparation.

The peptide-metal complexes described herein may also be used in combination with one or more other factors that improve treatment or prevention of skin cancers, such as, e.g., conventional topical chemotherapy such as imiquimod or 5-fluorouracil. In this manner, an additive or a synergistic effect may be obtained that provides a clinical efficacy better than that obtained with any single factor. Such factors can be selected for utilization in combination with the peptide-metal complex according to the therapeutic needs of the patient.

Types of skin neoplasm or cancer lesions which can be treated and resolved, or further development inhibited, according to the present invention include basal cell carcinoma, squamous cell carcinoma, malignant melanoma, dermatofibrosarcoma protuberans, Merkel cell carcinoma, Kaposi's sarcoma, keratoacanthoma, spindle cell tumor, sebaceous carcinoma, microcystic adnexal carcinoma, atypical fibroxanthoma, leimyosarcoma, and angiosarcoma.

The peptone-ionic metal complexes for use in the present the invention may be administered for therapeutic uses to humans or in veterinary applications to other warm-blooded animals. Among veterinary animals particularly well suited for treatment with the present compositions are species of equine, bovine, porcine, ovine, caprine, canine, avian, feline, etc. Among equines, older horses with dilute coat color, such as white or gray ("gray horses"), are particularly susceptible to melanoma and find benefit from treatment of the lesions according to the present invention.

Thus, the compositions are administered to a warm-blooded animal, such as human or horses, already suffering from a cancerous or pre-cancerous skin lesion or prophylactically after surgery to prevent or inhibit reoccurrence of the cancer or pre-cancerous lesion. Amounts adequate to accomplish these effects are defined as a "therapeutically effective doses." Amounts effective for this use will depend on the severity of the lesion but generally range from about 0.1 mg to about 50 mg per day of peptide-metal complex per day per square centimeter of lesion or surgical site, with dosages of from about 10 mg to about 25 mg per day per square centimeter of lesion site being more commonly used. The lesions should be monitored for response and administration of the preparations adjusted as needed. Maintenance dosages over a prolonged period of time may be adjusted as necessary.

For veterinary uses higher levels may be administered as necessary. Determining precise amounts of the peptide-metal necessary to treat a particular cancerous or pre-cancerous condition or lesion on an individual as described herein will be through empirical methods well known in the medicinal art.

In prophylactic applications, compositions containing the peptide-metal complexes are administered to a host susceptible to or otherwise at risk of cancerous skin lesions or similar pathology, particularly at sites following surgical resection of a previous lesion. Such an amount is defined to be a "prophylactically effective dose." In this use, the precise amounts again depend on the host's condition and general state of health, but generally range from about 0.1 mg to about 10 mg per day per square centimeter of skin, more commonly from about 1 mg to about 3 mg per $cm^2$ of skin per day. Single or multiple administrations of the compositions can be carried out.

The peptide-metal complexes of the invention may be administered in relatively large amounts without serious side effects, although indiscriminate use may produce discoloration of the skin.

The following examples are offered to illustrate, but not to limit, the claimed invention.

EXAMPLES

Using Mixed Peptide Copper Complexes on Horse Melanomas

For these studies enzymatically digested soy proteins were used. The enzymatic digests produce a mixture of many small peptides of 300 to 700 molecular weight. These were chelated with copper chloride to produce copper peptides, then blended into a cream base for application. The methods of preparation are described in U.S. Pat. Nos. 5,382,431; 5,554,375; and 5,888,522, incorporated herein by reference. These peptide digests are very resistant to further proteolytic breakdown by enzymes. When wet, they are very adhesive to skin, essentially forming a glue that is similar to traditional animal protein hydrolyzed collagen glues which have been used for over 8,000 years.

When tested on horses, these types of copper peptides were surprisingly effective at removing the skin cancers without any toxic actions.

An eight-year old Gray Horse with a small melanoma, about 6 cm diameter, was treated with the mixed peptide (peptone) copper complex cream five times per week for six weeks. The cream was rubbed into the skin on the melanoma. The melanoma became progressively smaller and vanished at around 7 weeks. It did not visibly reoccur during the following two years.

An eleven-year old Gray Horse with a small melanoma, about 4 cm diameter, was treated with a cream of the copper-peptone complex seven times per week for six weeks. The cream was rubbed into the skin of the melanoma. The melanoma became progressively smaller over the six weeks but still remained. The treatment was continued for another 4 weeks and the melanoma vanished. It did not reoccur during the following year.

Treatment of Human Basal Cell Carcinomas

The three human skin cancers treated were all re-occurring basal cell carcinomas on the head and/or neck. All three people had undergone repeated but successful procedures to remove such lesions. Since this type of cancer is of relatively low risk, these individuals tried a high strength mixed (peptone) peptide-copper cream on a new lesion.

A 47-year old woman had a history of repeated basal skin cancer lesions. Previous lesions had been surgically removed. She applied the copper peptide cream to the lesion each day. The lesion became progressively smaller by one month. She continued the treatment for another two months and the lesion vanished. It did not reoccur over the next year.

A 64-year old man had a history of repeated basal skin cancer lesions. Previous lesions had been surgically removed. He applied the copper peptide cream each day to the lesion. The lesion became progressively dryer and smaller. After 7 weeks, the lesion vanished. It did not reoccur over the next year although the outline of the lesion remained on the skin's surface.

A 59-year old man had a history of repeated basal skin cancer lesions. Previous lesions had been surgically removed. He applied the copper peptide cream each day to the lesion. The lesion became progressively dryer and smaller. After three months the lesion vanished. It did not reoccur over the next year.

While the preferred embodiments of the invention have been illustrated and described, it will be appreciated that various changes can be made therein without departing from the spirit and scope of the invention.

The embodiments of the invention in which an exclusive property or privilege is claimed are defined as follows:

1. A method for treating a skin cancer on an individual, comprising administering topically to the cancer lesion a therapeutically effective amount for a duration sufficient to treat the skin cancer of a composition which comprises a peptone-ionic metal complex wherein the metal is copper(II) and a topically acceptable carrier.

2. The method of claim 1, wherein the skin cancer is a basal or squamous cell carcinoma.

3. The method of claim 1, wherein the skin cancer is malignant melanoma.

4. The method of claim 1, wherein the skin cancer is dermatofibrosarcoma protuberans, Merkel cell carcinoma, Kaposi's sarcoma, keratoacanthoma, spindle cell tumor, sebaceous carcinoma, microcystic adnexal carcinoma, atypical fibroxanthoma, leimyosarcoma, or angiosarcoma.

5. The method of claim 1, wherein the composition is administered topically on a daily basis to the skin cancer lesion in which resolution or inhibition is desired.

6. The method of claim 1, wherein the peptone is a peptone digest prepared from casein, collagen, elastin, meat protein, silk protein, or soybean protein.

7. The method of claim 1, wherein the peptone-ionic metal complex of the composition has been sterilized or pasteurized.

8. The method of claim 1, wherein the composition is applied as a cream, lotion, gel or salve.

9. The method of claim 1, wherein the concentration of the peptone-ionic metal complex in the topical composition is about 1% to 25%.

10. The method of claim 1, wherein the individual is a human.

11. The method of claim 1, wherein the composition is formulated for veterinary administration.

12. The method of claim 11, where the veterinary administration is for equine, bovine, feline, porcine, caprine, ovine or canine species.

13. A method for treating a melanoma on a horse, comprising administering topically to a melanoma lesion a composition which comprises a peptone-ionic metal complex wherein the metal is copper(II) and a topically acceptable carrier in a therapeutically effective amount and for a duration sufficient to treat the melanoma.

14. The method according to claim 13, wherein the composition is administered to the lesion at least three to five days a week for six weeks.

15. A method for treating a basal cell carcinoma on an individual, comprising administering topically to the lesion of the carcinoma a composition which comprises a peptone-ionic metal complex wherein the metal is copper(II) and a topically acceptable carrier in a therapeutically effective amount and for a duration sufficient to treat the carcinoma.

16. The method according to claim 15, wherein the carcinoma lesion is a site of a prior surgical removal of the carcinoma.

* * * * *